United States Patent [19]

Newman et al.

[11] Patent Number: 5,616,329

[45] Date of Patent: Apr. 1, 1997

[54] SPRAY-DRIED ANTIGENIC PRODUCTS

[75] Inventors: Stephen G. Newman; William W. Kay, both of Victoria, Canada

[73] Assignee: Microtek Research and Development Ltd., Saanichton, Canada

[21] Appl. No.: 270,526

[22] Filed: Jul. 5, 1994

Related U.S. Application Data

[63] Continuation of Ser. No. 621,836, Dec. 4, 1990, abandoned.

[51] Int. Cl.$^6$ .................. A61K 39/106; A61K 39/02; A61K 9/14; A01N 63/00

[52] U.S. Cl. ..................... 424/261.1; 424/184.1; 424/234.1; 424/237.1; 424/241.1; 424/827; 424/249.1; 424/250.1; 424/278.1; 424/93.48

[58] Field of Search .................. 424/184.1, 261.1, 424/93.48

[56] References Cited

U.S. PATENT DOCUMENTS

| | | | |
|---|---|---|---|
| 2,710,810 | 6/1955 | Strashun | 435/260 |
| 2,908,614 | 7/1959 | Muggleton et al. | 167/78 |
| 3,492,400 | 4/1970 | Klontz | 424/92 |
| 3,608,066 | 4/1971 | Illartein | 424/46 |
| 3,755,557 | 3/1973 | Jacobs et al. | 424/46 |
| 3,862,313 | 1/1975 | Fryer et al. | 424/92 |
| 3,911,109 | 10/1975 | Kenworthy | 424/92 |
| 3,988,440 | 10/1976 | Bogdanor | 424/115 |
| 4,009,259 | 3/1977 | Ament et al. | 424/89 |
| 4,223,014 | 7/1980 | Garrison et al. | 424/92 |
| 4,287,179 | 9/1981 | Amend | 424/92 |
| 4,734,401 | 3/1990 | Bloun | 514/14 |
| 4,904,477 | 2/1990 | Ho et al. | 424/498 |
| 5,017,372 | 5/1991 | Hastings | 424/85.8 |

FOREIGN PATENT DOCUMENTS

| | | |
|---|---|---|
| 153382 | 7/1904 | Germany. |
| 1144215 | 3/1969 | United Kingdom. |
| WO82/02491 | 2/1982 | WIPO .......... A61K 39/02 |

OTHER PUBLICATIONS

Braude et al Infect Dis & Med. Microb. 1986 p. 59.
Splittstoesser et al Applied Microbiology vol. 5 1957 pp. 333–339.
Kawai et al Bull Jpn. Soci Fish 49: 511–514 1983. Effecacy of the Lipo–poly sacchaude vaccine against Vibrosis in Cultured AYN Plecoglossus–Altivelis (Abstract only).
Biological abstracts, vol. 81, 1986, Philadelphia, Chun, S. K. et al.: "Immune Response of the Japanese Eel (Anquilla Japonica) to Vibrio Anguillarum" & Bull Korean Fish SOc. 18(5), 464–470, 1985, Abstract number 72521.
International Search Report from the European Patent Office, date of mailing: Feb. 27, 1992.
Pelczor et al McGraw–hill Book Co. 1953 pp. 200–215.
Kawai et al. Bulletin of the Japn Soc. of Scientific fisheries.
Moore et al J. Food Protection 51: 565–568 1988 Abstract. Changes in Bacterial Cell & Spore counts of reduced–Fat Egg Products as influenced by Postenerization & spray drying.
Rahn, Bacteriological Reviews, 9:1–47, 1945.
Kawai et al, Bull Jpn Soc Sci Fish 49:571–574 1983.
McLain Dissertation Abstracts pp. 1872–1873 vol. XVI, No. 10, 1956.
McLain Dissertation Abstract p. 629.

*Primary Examiner*—Hazel F. Sidberry
*Attorney, Agent, or Firm*—Klarquist Sparkman Campbell Leigh & Whinston, LLP

[57] ABSTRACT

A method is described for preparing an antigenic product which incorporates exposing an aerosol of a microbial suspension to temperatures at which substantially only the heat stable components of the microbial suspension which retain their immunogenic properties remain. More specifically, the aerosol is exposed to an elevated temperature which denatures all labile components and removes the liquid portion of the aerosol by evaporation.

10 Claims, No Drawings

SPRAY-DRIED ANTIGENIC PRODUCTS

This application is a continuation of application Ser. No. 07/621,836, filed on Dec. 4, 1990, now abandoned.

FIELD OF THE INVENTION

This invention relates to vaccines or antigenic compositions and methods of preparation thereof. These methods are particularly useful for preparing animal vaccines, more specifically fish vaccines.

BACKGROUND OF THE INVENTION

Vaccines and/or bacterins (formalin inactivated whole cell suspensions) are widely used to prevent diseases in humans and other animals. They usually consist of the organism and/or its metabolites responsible for a particular disease problem. The organisms may be in either their natural form, dead whole cells or live or attenuated or in non-native forms comprised of structural subunits of the pathogen or crucial metabolites. Almost all gram negative bacteria have a heat stable cell wall structural component referred to as lipopolysaccharide (LPS), that may function as a protective antigen. That an immune response directed against these structural components is sufficient to protect the animal against subsequent challenge by the pathogen. As with other animals, fish reared for food also suffer from systemic diseases that require prevention and/or treatment.

These diseases are due to variety of pathogens, including viruses, bacteria, fungi, protozoans and metazoans. The types of diseases depend upon geography (where the fish are being reared), genetics (the species and genetic makeup), the environment (i.e., fresh versus brackish versus salt water) and the management/husbandry philosophies of those individuals rearing the fish. Disease prevention is always preferable to reactive disease treatment. Many of the primary bacterial pathogens that affect fish can readily be prevented by immunization.

Fish vaccines generally consist of formalin inactivated suspensions of whole cells. These preparations are diluted and administered to fish by injection or immersion. Alternative methods include bathing the fish in highly dilute suspensions or spraying fish directly with the diluted preparation, which is then absorbed through the gill membranes.

Virtually all commercially available fish vaccines are in liquid form and are prepared by either continuous culture or batch fermentation and are subsequently inactivated with formaldehyde. They are whole cell-based products that depend on a stable cell wall component (LPS) for their protective properties. Due to their liquid nature, these products have strict refrigeration requirements. Accordingly, a relatively short shelf-life can be expected and the products may become contaminated with extraneous organisms or even occasionally with living organisms contained in the vaccine, particularly if the container of the liquid product is opened and resealed improperly. The liquid products are also bulky and inconvenient to transport in large quantities. Furthermore, the use of liquid based bacterins in oral vaccine preparations may be hampered by rancidity problems, standardization of antigen levels and stability problems.

Exemplary of the currently available methods for the preparation of vaccines are the following:

U.S. Pat. No. 3,862,313 to Fryer et al. describes a wet whole cell vaccine of *Vibrio anguillarum* which may be administered orally or by injection. The actual preparation of the vaccine comprises growing the bacterial cells in a suitable medium, killing the cells by formaldehyde addition, harvesting the cells by centrifugation and finally freezing the resultant wet cells. For use, the frozen vaccine is thawed into a paste.

U.S. Pat. No. 3,755,557 to Jacobs teaches the use of lecithin as a stabilizer to disperse dry antigens in a liquid propellant for spray vaccines. The antigens must be worked up into the vaccine in a dry condition. The techniques of freeze-drying and vacuum drying are described.

U.S. Pat. No. 3,608,066 to Illartein describes a pharmaceutical preparation of finely ground, killed, lyophilized microorganisims and a suitable carrier. It is designed to be used in the upper and lower respiratory tracts. The preparation of the antigenic component includes heat killing and centrifuging the chosen bacteria, lysing the cells and then lyophilizing the resultant suspension by conventional means. The powdered antigen is then prepared into an aerosol formulation with a lubricant and a propellant.

U.S. Pat. No. 4,287,179 to Amend provides a liquid vaccine in which whole fish are immersed which comprises killed *Yersinia ruckeri*.

It is an object of the present invention to obviate or mitigate the above disadvantages.

SUMMARY OF THE INVENTION

The present invention provides a method of preparing an antigenic product which comprises exposing an aerosol of a microbial suspension to temperatures at which substantially only the heat stable components of the pathogen culture which retain their immunogenic properties remain. More specifically, the aerosol is initially exposed to a temperature at which substantially only the heat stable components of the microbial suspension remain immunogenic and subsequently the components are cooled to a second, lower temperature prior to harvesting the product so formed.

This method is suitable for preparing vaccines which are lipopolysaccharide (LPS) based, that is, those in which LPS comprises the primary protective antigen. The method is also suitable for preparing vaccines based upon any heat stable antigenic determinants. This method is particularly useful in preparing animal including, but not limited to, fish vaccines.

The method of preparation described herein will be referred to as the "spray-drying" method. Also included within the scope of the present invention are the antigenic products formed by the methods described herein.

The antigenic products of the present invention are particules and retain their biological activity after prolonged storage even in non-refrigerated conditions. Therefore, unlike the previous liquid based products, they do not appear to have a date limitation. This stability makes the product invaluable in environments where refrigeration is unavailable and significantly reduces the cost associated with transporting the product. With respect to the immunization of fish, the heat stability of the antigenic products of the present invention makes them attractive candidates for milling into feeds where significant heat can be generated during the milling process. Furthermore, due to the very low moisture content, the antigenic products are resistant to contamination with bacteria and/or viable fungi.

Pathogenic cells contained in conventional freeze-dried vaccine preprations retain their structural integrity. Were it not for treatment with formaldehyde, these cells would remain viable. In contrast, cells under going the spray-drying process of the present invention are rendered structurally different from the starting material. This structural alteration is due to the heating step within the process which denatures the majority of proteins found in the cells. In doing so, the cells are rendered non-viable.

PREFERRED EMBODIMENTS OF THE INVENTION

In a preferred form, the method of the present invention comprises forming an aerosol of a microbial suspension, exposing the aerosol to an initial temperature at which substantially only the heat stable components of the microbial suspension retaining immunogenicity remain, cooling the components to a second temperature which is lower than the first temperature and harvesting the product so formed.

The aerosol of the microbial suspension may be formed by any suitable method, but preferably, it is formed by forcing, under pressure, the suspension through a nozzle with a suitably small aperture.

The first temperature to which the aerosol is exposed should be sufficient to substantially denature the proteins and other labile components of the microbial suspension leaving substantially only the heat stable components. This temperature will depend to some extent on the particular pathogen and may be readily ascertained by routine experimentation. Most preferably, the first temperature is between 100°–160° C. Coincident with denaturing the microbial proteins is the process of evaporating the liquid from the suspension.

The second temperature, created by the evaporation process, is lower than the first temperature but should preferably not be less than 70° C. although this may vary with respect to different pathogens. Most preferably, the second temperature is between 70°–100° C.

In a preferred form, the microbial suspension is concentrated prior to the spray-drying process by any number of conventional techniques (for example, centrifugation). The concentrated suspension is then dispersed in the form of an aerosol into a chamber having a heated inlet (first temperature) and an outlet (second temperature). The water in the suspension is evaporated in the drying process and substantially, only heat stable antigenic product remains in the chamber. The resultant powdered product is harvested and is suitable without further modification for use as a vaccine.

In a preferred form, the aperature size is 0.5 mm but can be adjusted to compensate for a scaled-up process.

In a preferred form, the rate of flow through the chamber is adjusted such that the particle retention time is less than 1 (one) second.

In a preferred form, the microbial suspension is inactivated by standard methods of the art such as the addition of formaldehyde prior to aerosol formation. This inactivation step is preferred but not required because the heat (first temperature) in the process renders the cells non-viable.

Carriers or adjuvants may be added to the dried antigenic product prior to vaccine formation.

The method of the present invention is particularly suitable for the preparation of LPS or heat stable antigen based animal vaccines. The pathogens listed herein are merely intended to be exemplary of those suitable for use in the preparation of spray-dried antigenic products. The list includes Vibrio anguillarum, Vibrio ordalli and Vibrio salmonicida.

The method herein is suitable but not exclusive for the preparation of antigenic products to fish pathogens. The powdered antigenic product formed by the present method may be used to immunize fish in several ways; orally, by injection or by immersion. The most economically viable method of immunization is the mixing of the powdered antigenic product with an oil base, which can then either be used to coat the surface of prepared feed or milled directly into the feed during its manufacture.

The antigenic products of the present invention may also be used to immunize crustanceans, particularly shrimp. It is believed that the immune system of shrimp is non-specific and, therefore, random vaccination against one pathogen may lead to immunity against many others.

The following examples are provided to illustrate various aspects of the present invention, but are not intended to be limiting in any way.

EXAMPLES

Example 1: Preparation of a vaccine for spray drying

A pure culture of the bacterial fish pathogen, Vibrio anguillarum, was used to generate a large volume suspension of V. anguillarum by batch fermentation (continuous culture fermentation may also be used). The exact fermentation parameters depend on the organisms and strains employed. After the fermentation reached the desired endpoint, usually determined by biomass, the bacterial culture was inactivated using standard methods in many, but not all, cases, by the addition of 0.3 to 0.6% formaldehyde. The fermentor vessel was then used to agitate the mixture. After enough time had passed to allow for inactivation of the bacterial culture (12–36 hours), the cell mass was harvested by centrifugation. The use of concentrated materials is not in itself critical to the spray drying process itself but relates only to the time involved in processing the materials.

The bacterin was then pumped through a commercial spray drier—Niro Atomizer, serial #8410 which was fitted with a size 4 nozzle (0.99 um diameter). The vaccine was pumped through this nozzle. The water in the bacterin was evaporated as the vaccine was deposited on the walls of the spray drying vessel. This spray dried material was then harvested as discussed herein. The bacterin was exposed to a temperature of no less than 70° C. and no higher than 160° C. during the drying process. The powdered product was packaged and tested.

Example 2: Oral application of the spray dried bacterin

| Organism[1] | Method of Vaccination[2] | Dosage[3] | Results (mortality)[4] Control | Vaccinates |
|---|---|---|---|---|
| VA | Oral | 2 mg/gram diet 10 feedings 2%/day top dress | 73% | 17% |
|  | Oral | 5 mg/gram feed 10 feedings 2%/day milled into feed | 100% | 11% |

[1] - VA-Vibrio anguillarum.
[2] and [3] - Fish were fed the vaccine either mixed in oil and mixed manually onto feed referred to as top dressing or milled into the feed when the feed was manufactured.
[4] - N = 30; approximately 14 days post vaccination, the fish were exposed to a virulent suspension of Vibrio anguillarum by being bathed in 5 × 10⁶ CFU/ml for 20 min. A group of fish that were fed a diet that had been handled exactly the way that the experimental diets were - i.e. top dress-coated with oil containing no bacterin, milled-same diet except with no vaccine in it were the control fish. These fish were challenged using the same culture and under the same conditions as the vaccinates were. The values expressed here are based on thirty fish samples and reflect the numbers of fish dying up to 14 day post challenge.

Example 3: Immersion vaccination with a spray dried bacterin

| Organism[1] | Method of Vaccination[2] | Dosage[3] | Results (mortality)[4] Control | Vaccinates |
|---|---|---|---|---|
| VA | Immersion | 5 mg/ml 20 sec. | 68% | 0% |
|  | Immersion | 5 mg/ml 20 sec. | 100% | 17% |

Example 3: Immersion vaccination with a spray dried bacterin

| Organism[1] | Method of Vaccination[2] | Dosage[3] | Results (mortality)[4] Control | Vaccinates |
|---|---|---|---|---|
| VO | Immersion | 5 mg/ml 20 sec. | 68% | 0% |

[1] - VA-*Vibrio anguillarum*; VO-*Vibrio ordalii*.
[2] and [3] - The fish were immunized by being immersed in a suspension of the material at a concentration of 5 mg of bacterin/ml of water for 20 seconds duration.
[4] - Approximately 14 day post vaccination the fish were challenged by being exposed to virulent pathogens. Refer to Example 2 for procedure used with *Vibrio anguillarum*. For *Vibrio ordalii*, the fish were injected intraperitoneally with approximately $10^6$ bacteria and observed for 14 days.

Example 4: Stability testing of a spray dried vaccine.

| Organism[1] | Method of Vaccination[2] | Dosage[3] | Control | Results (mortality)[4] Vaccinates |
|---|---|---|---|---|
| VA | Immersion (2 yr stability) | 5 mg/ml 20 sec. | 73% | 0% |

[1] VA - *Vibrio anguillarum*.
[2] and [3] - The bacterin had been on the shelf for two years (room temperature - mean approximately 20° C.) and was tested by immersion using the same protocol as described in Example 3.
[4] - See previous examples for explanation.

Example 5: Evidence of duration of immunity

| Organism[1] | Method of Vaccination[2] | Dosage[3] | Control | Results (mortality)[4] Vaccinates |
|---|---|---|---|---|
| VA | Immersion (156 days post vaccination) | 5 mg/ml 20 sec. | 71% | 20% |
| VO | Immersion (180 days post vaccination) | 5 mg/ml 20 sec. | 90.6% | 38% |
|  | Immersion (114 days post vaccination) | 5 mg/ml 20 sec. | 100% | 40% |

[1] - VA-*Vibrio anguillarum*; VO-*Vibrio ordalii*.
[2] and [3] - The fish were immunized by being immersed in a suspension of the material at a concentration of 5 mg of bacterin/ml of water for 20 seconds duration.
[4] - At the number of day indicated post vaccination the fish were challenged by being exposed to virulent pathogens. Consult previous examples for procedure used with both organisms.

We claim:

1. A method of preparing a vaccine from a suspension of pathogenic bacteria possessing lipopolysaccharide, the method comprising:

providing a culture of the bacteria;

inactivating the bacteria;

spray drying the inactivated bacteria at a temperature sufficient to denature substantially all heat-labile components of the bacterial culture; and harvesting a dried vaccine product.

2. The method of claim 1 wherein the inactivation step comprises adding a sufficient amount of formalin to the bacterial culture.

3. The method of claim 1 wherein the spray drying step comprises:

aerosolizing the culture of bacteria; and exposing the aerosolized bacterial culture to a temperature sufficient to evaporate substantially all liquid from the suspension.

4. The method of claim 3 wherein the temperature is between 100° and 160° C.

5. The method of claim 1 wherein the bacterial culture is concentrated prior to spray drying.

6. A method of preparing a dried vaccine from a suspension of pathogenic bacteria possessing lipopolysaccharide, the method comprising:

inactivating the bacterial suspension;

aerosolizing the bacterial suspension;

exposing the aerosolized suspension to a first temperature of 100°–160° C.; and harvesting a dried antigenic vaccine product.

7. The method of claim 6 wherein prior to harvesting the aerosolized suspension is exposed to a second temperature of 70°–100° C.

8. The method of claim 6 wherein the pathogenic bacteria are selected from the group consisting of: *Vibrio anguillarum*, *Vibrio ordalli*, and *Vibrio salmonicida*.

9. The method of claim 1 wherein the pathogenic bacteria are selected from the group consisting of: *Vibrio anguillarum*, *Vibrio ordalli*, and *Vibrio salmonicida*.

10. A method of preparing a dried vaccine comprising:
providing a suspension of bacteria selected from the group consisting of *Vibrio anguillarum*, *Vibrio ordalli*, and *Vibrio salmonicida*;

inactivating the bacteria;

forming an aerosol of the suspension;

exposing the aerosol to a first temperature of between and 160° C.;

exposing the aerosol to a second temperature of between 70° and 100° C.; and harvesting a dried vaccine product.

* * * * *